United States Patent [19] [11] 4,222,380
Terayama [45] Sep. 16, 1980

[54] CELIAC INJECTOR
[75] Inventor: Toshiki Terayama, Kodaira, Japan
[73] Assignee: Olympus Optical Co., Ltd., Tokyo, Japan
[21] Appl. No.: 44,569
[22] Filed: Jun. 1, 1979
[30] Foreign Application Priority Data
  Dec. 2, 1977 [JP] Japan ................. 52-162023
[51] Int. Cl.³ .............................. A61M 5/00
[52] U.S. Cl. ........................ 128/216; 128/4
[58] Field of Search ........... 128/216, 215, 221, 325, 128/348, 4, 346
[56] References Cited
U.S. PATENT DOCUMENTS

| 2,704,071 | 3/1955 | Becker | 128/346 X |
|---|---|---|---|
| 3,659,610 | 5/1972 | Cimber | 128/215 |
| 3,884,220 | 5/1975 | Hartnett | 128/215 X |
| 4,043,323 | 8/1977 | Komiya | 128/4 |
| 4,162,678 | 7/1979 | Fedotov et al. | 128/325 |

*Primary Examiner*—John D. Yasko

[57] ABSTRACT

Disclosed is a celiac injector introduced into a body cavity by means of an endoscope, thereby injecting a medical fluid into desired celiac tissue, in which a medical fluid supply tube with an injector needle fixed to the tip end thereof and an elongated member fitted at its tip end with a plurality of claw wire elements are relatively slidably housed in an outer sheath. By manual operations of the respective proximal end portions of the supply tube and elongated member, the claw wire elements take hold of a tissue portion at a desired part, the needle is stabbed into the held tissue portion, and the medical fluid supplied through the supply tube is injected into the tissue by means of the injector needle.

9 Claims, 6 Drawing Figures

CELIAC INJECTOR

BACKGROUND OF THE INVENTION

This invention relates to a celiac injector introduced into a body cavity by means of an intra-celiac medical instrument such as an endoscope, whereby a medical fluid is injected into celiac tissue at a desired part inside the body cavity.

The elongated injector of this type, like catheters and other intra-celiac medical instruments, is inserted in a channel of an endoscope, for example. The distal end portion of the injector may be brought into the body cavity by introducing a flexible tube of the endoscope into the body cavity for medical observation and examination of celiac tissue. In injecting a medical fluid into tissue at part detected during the endoscopic observation, the distal end of the injector is extended beyond an open end of the flexible tube of the endoscope to be brough close to the objective part. Subsequently, an injector needle is projected from the distal end of the injector and stabbed into the tissue, and then the medical fluid is injected into the tissue.

Thus, the distal end portion of the injector is guided to the objective part inside the body cavity by the endoscope. Even if guided accurately to the objective part, however, the injector will be wrongly stabbed or not be stabbed at all due to slipping of the needle point if the tissue to be stabbed with the needle is too hard or too soft. Moreover, even through the needle is stabbed into the correct part, the needle point may be removed from the tissue during the injection of the medical fluid.

If the celiac part to be stabbed exists in an internal organ always in drastic motion or is a quite narrow portion or a small projecting portion, in particular, then the aforesaid difficulties will be augmented.

SUMMARY OF THE INVENTION

Accordingly, the object of this invention is to provide a celiac injector capable of secure stabbing of an injector needle and injection of a medical fluid into a part inside a body cavity without involving slippage or removal of a needle point as against the celiac tissue.

In order to attain the above object, there is provided an injector of the following construction. That is, inside an outer sheath, an elongated, flexible tubular member for drive transmission is disposed between the outer sheath and a supply tube, a slider being attached to the proximal end portion of the member. The transmission member may be moved relatively to the outer sheath and the supply tube along the longitudinal direction by manually operating the slider. A claw means, which is attached to the distal end of the transmission member, is projected outward from an open distal end of the outer sheath to catch and hold tissue at a part to be injected inside a body cavity prior to an injecting operation. Then, an injector needle is stabbed into the caught celiac tissue to inject a medical fluid thereinto.

Thus, the desired part is securely grasped by the claw means, so that the injector needle surely be inserted without slipping independently of the hardness of the tissue. During the injecting operation, the tissue portion can be continuously, steadily held by the claw means, eliminating the conventional shortcomings such as removal of the needle in the middle of the operation.

According to a preferred embodiment of the invention, the claw means is formed of two of more wire elements whose proximal ends are fixed to the distal end of the drive transmission member and whose tip ends extend longitudinally so as to surround the needle and are radially curved so as to be gradually separated from one another. The middle portions of the elements are pressed against the peripheral edge of the open distal end of the outer sheath by their own springy property. When these elements are so moved as to be drawn into the other sheath, the hook-shaped tip ends of the elements are brought close to one another along the radial direction to catch hold of the celiac tissue. When the elements are so driven as to come forward from the outer sheath, on the other hand, the hook-shaped tip ends are separated radially from one another to be restored by the spring action of the middle portions, and release their hold of the celiac tissue.

Thus, the claw means formed of a plurality of wire elements does not require any special spring member for the holding and releasing of the tissue.

Also, the claw means may be formed of elements of any shape other than the wire elements. In any case, however, the proximal ends of the elements are fixed to the distal end of the drive transmission member, and their tip ends are separated from one another, spreading out together in the form of a funnel or trumpet. The injector needle is located along the central axis of such funnel or trumpet.

The injector needle may, therefore, be stabbed into the central portion of the celiac tissue grasped by the claw elements. Thus, the needle may securely be stabbed even into a part of an internal organ that is continuously in motion.

DETAILED DESCRIPTION OF THE PREFERRED EMBODIMENTS

Now there will be described preferred embodiments of the present invention with reference to the accompanying drawings.

Figure 1:
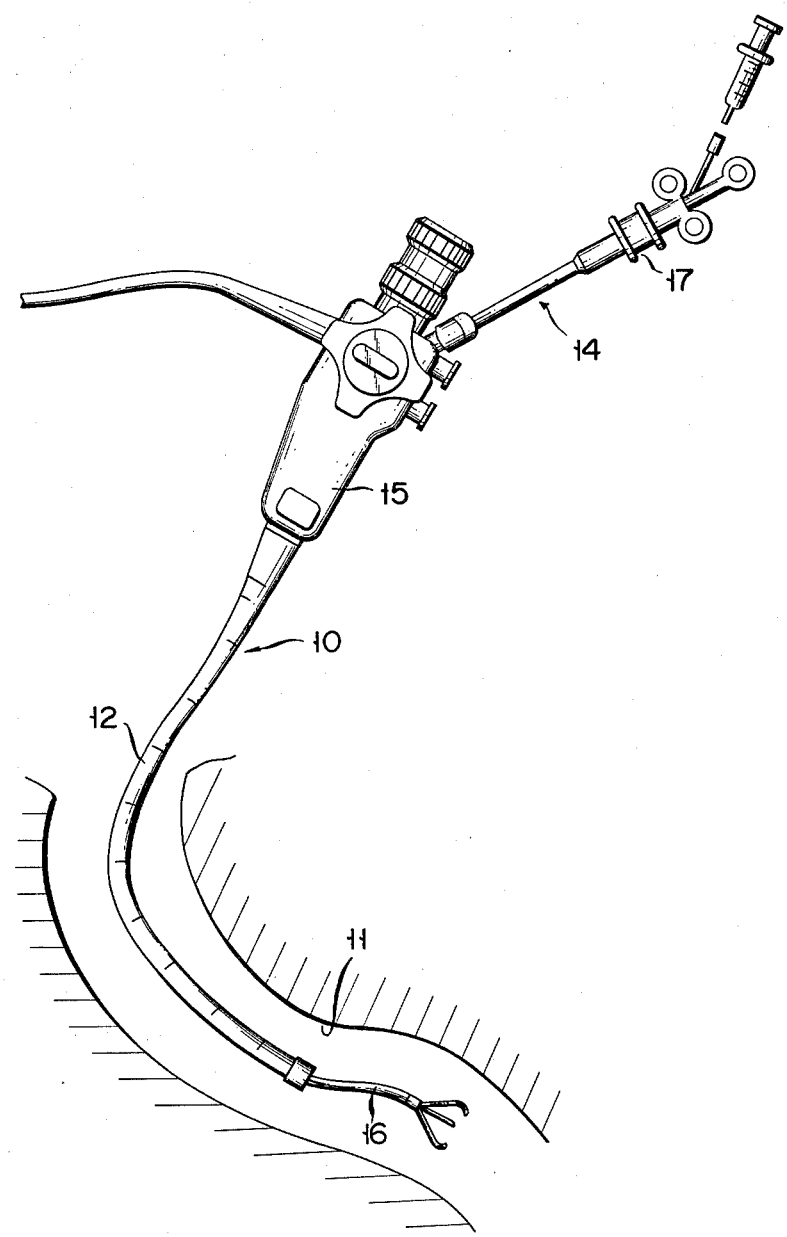
FIG. 1 is a schematic view of a celiac injector according to this invention which is inserted in an endoscope and introduced into a body cavity under the guidance of the endoscope.

In FIG. 1, an endoscope 10 is of well-known construction, including a flexible tube 12 which is to be introduced into a human body cavity 11 such as stomach or bowel. Inside the tube 12 is a channel 13 (indicated by chain lines in FIG. 3) through which a catheter or some other intra-celiac medical instrument is passed.

Like the catheter and other instruments, a celiac injector 14 according to this invention is also inserted into the channel 13 of the endoscope 10 through an inlet at a control section 15, and guided by the endoscope 10 to reach a part to be examined inside the body cavity 11.

The celiac injector 14 is formed of a flexible, elongated outer sheath 16 and an operator-operative driving section 17 at the proximal end of the sheath.

Figure 3:
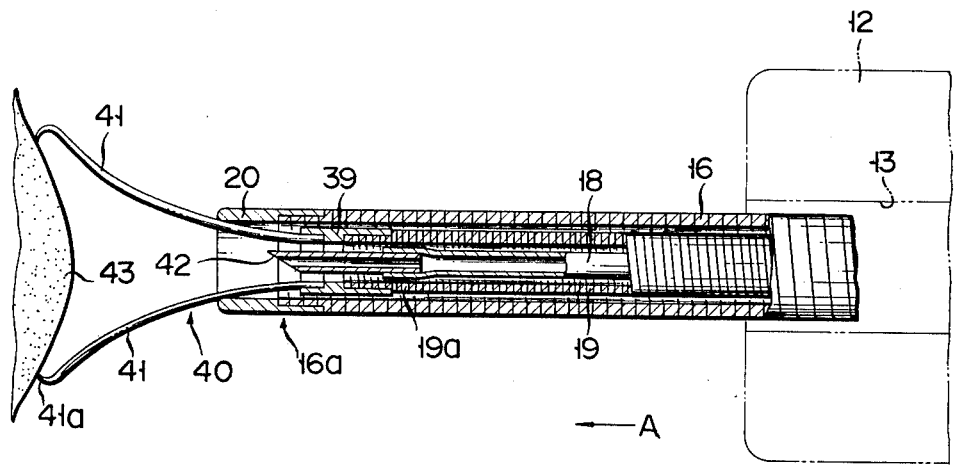
FIG. 3 is a profile of a distal end section of the celiac injector in which the distal end of a flexible tube of the endoscope is suggested by chain lines.
Figure 4:
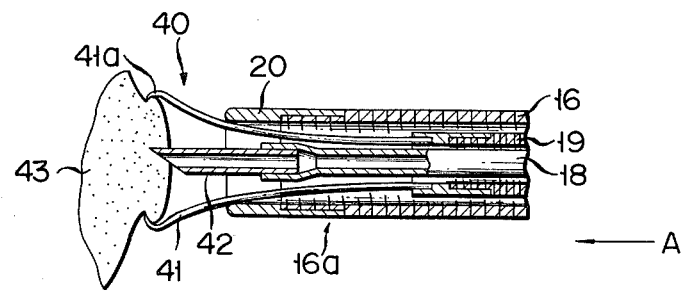
FIG. 4 is a profile of the distal end section of FIG. 3, showing such a situation that a portion of celiac tissue, grasped by the distal end section, is about to be injected.

In the sheath 16, two flexible, elongated members or tubes 18 and 19 are inserted in the form of a double pipe in the longitudinal direction of the sheath 16. The tubes 18 and 19 are used for medical fluid supply and drive transmission, respectively. The drive transmission tube 19 and the outer sheath 16 are formed by closely spirally winding thin tapelike or round wire. These tubes may, however, be formed of any other suitable material. The supply tube 18 is small and made of a metal or synthetic resin, such as Teflon. Further, these two tubes 18 and 19 can separately slide in the axial direction relatively to the outer sheath 16, as mentioned later. A metallic cover ring 20 is fixed to a distal end 16a of the outer sheath 16, forming an open distal end. The annular edge of the cover ring 20 is slightly rounded as shown in FIGS. 3 and 4.

Figure 2:
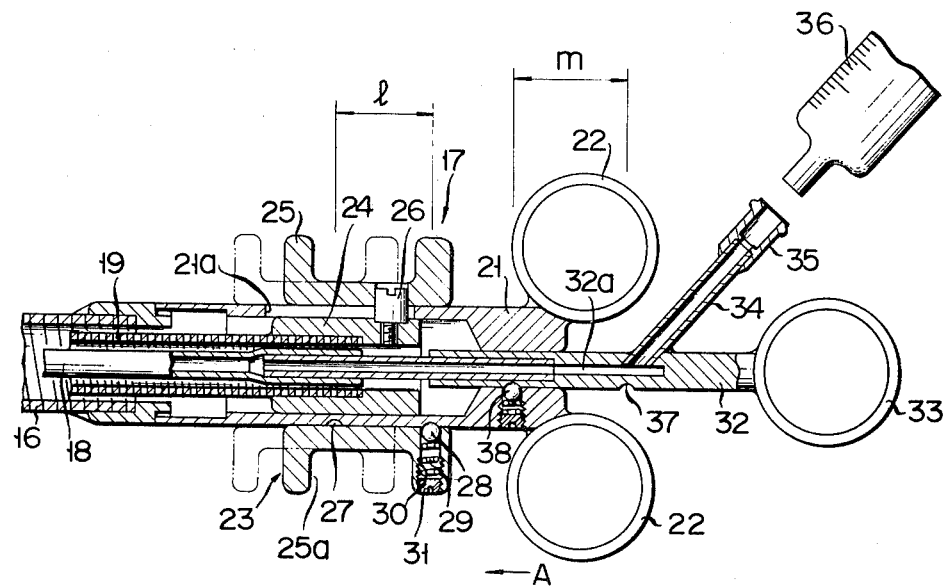
FIG. 2 is a profile of a proximal operative section of the celiac injector of the invention.

At the driving section 17 of the celiac injector 14 as shown in FIG. 2, a cylindrical grip member 21 is fixed to the proximal end of the outer sheath 16, and two finger rings 22 are formed in a body at one end of the grip member 21. The member 21 is provided with a slider 23 capable of sliding in the axial direction. An inner cylindrical section 24 of the slider 23 is fixed to the proximal end of the drive transmission tube 19, and coupled rigidly to an outer cylindrical section 25 of the slider by means of a screw 26. The head of the screw engages a slot 21a formed in the grip member 21 along the axial direction, thereby preventing the slider 23 from rotating relatively to the grip member 21. Thus the slider 23 is allowed to move only in the axial direction within a fixed range. On the outer peripheral surface of the outer section 25 of the slider is an annular grip groove 25a to be caught by operator's fingers.

In the cylindrical outer surface of the grip member 21, as shown in FIG. 2, are two hemispherical indentations 27 formed at an axial distance l from each other. Inside the outer section 25 of the slider, on the other hand, a ball 28 is radially urged toward the outer periphery of the grip member 21 by a coil spring 29. The urging force of the spring 29 may be adjusted by means of a stop 31 mating with a tapped hole 30. That is, when the ball 28 gets engaged with one of the hemispherical indentations 27, the slider 23 is located in a position relative to the grip member 21. If subjected to fairly great axial force, the ball 28 will get out of the indentation 27, and the slider 23 will slide over the distance l, when the ball 28 will click into the other indentation to relocate the slider 23. Namely, the ball and the indentation form a locating means for removable fixation.

The position of the slider 23 indicated by full line in FIG. 2 will hereinafter be referred to as the backward position and the slider 23 can move forward as shown by chain line in FIG. 2. Arrow A indicates the direction in which the injector advances into the body cavity.

An inner cylindrical bore (denoted by no reference numeral) of the grip member 21 has its one end fixed to the proximal end of the medical fluid supply tube 18 and the other end axially slidably fitted with a driving member 32 with a finger ring 33. A guide bore 32a is formed axially in the member 32. The open end of the bore 32a opens into the supply tube 18, while the blind end of the bore is connected at the side to a connecting pipe 34. A container 36 containing the medical fluid is removably attached to a hub 35 put on the free end of the connecting pipe. Usually, the container 36 is the cylinder of a conventional injector, as shown in FIG. 1. The driving member 32 constitutes a control means for advancing and retreating an injector needle 42 as mentioned later.

A hemispherical indentation 37 formed at an axial distance m from the driving member 32 and a ball 38 spring-urged into the grip member 21 constitute a locating means for removable fixation in the same manner as aforesaid. The injector needle 42 is in a backward position as shown in FIG. 3 with the driving member 32 at the position of FIG. 2.

At the tip end portion of the injector as shown in FIG. 3, the proximal ends of two wire elements 41 constituting a claw means 40 are rigidly fixed to a distal end 19a of the drive transmission tube 19 by means of a fitting ring 39, diametrically facing each others. The position of FIG. 3 is such that the wire elements 41 are projected from the open distal end 16a of the outer sheath 16. The wire elements 41 extend axially in the direction of arrow A, gradually radially separated from the axis so that hook portions 41a at their respective tip ends are at a long distance from each other. Thus, the wire elements 41 are so curved as to separate their tip ends, tending to move by their spring action. Therefore, the middle portion of each wire element 41 is always in engagement with the rounded annular edge of the cover ring 20.

The injector needle 42 is rigidly fixed to the distal end of the supply tube 18, the sharpened tip end portion of the needle moving on the axis of symmetry of the pair of diametrically facing wire elements 41. The needle 42 is normally in the backward position where it is entirely withdrawn in the outer sheath 16, as shown in FIG. 3.

Figure 6:
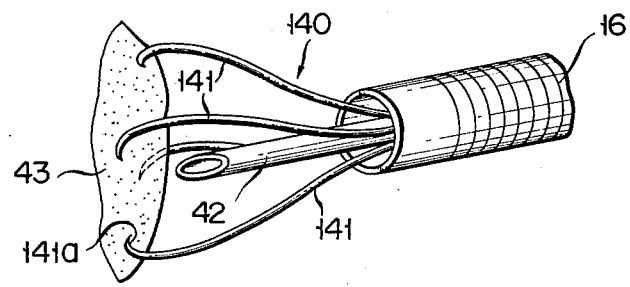

Wire elements constituting a claw means 140 may alternatively be more than two number as shown in FIG. 6 (four in this case). These wire elements 141 are arranged along the outer periphery of the injector needle 42 extending along the axis so as to surround the needle. Like the case of FIG. 3, the proximal ends (not shown) of the wire elements 141 are rigidly fixed to the distal end of the supply tube at regular circumferential angles, while the tip ends of the elements 141 spread out together in the form of a trumpet or funnel. The middle portions of all these elements 141 are outwardly spring-biased in the radial direction elastically to engage the outer peripheral edge of the open distal end of the outer sheath 16, in the same manner as shown in FIG. 3.

Figure 5:
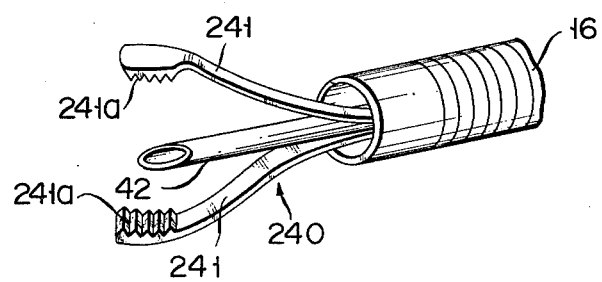
FIGS. 5 and 6 are perspective views of modifications of the distal end section, especially claw elements, of the celiac injector, showing different configurations.

FIG. 5 shows the construction of an alternative claw means 240 consisting of a pair of plate-like elements 241. Like the case of the wire elements 41 of FIG. 3, the proximal ends (not shown) of the elements 241 are rigidly fixed to the distal end of the supply tube, diametrically facing each other. The tip ends of the plate-like elements 241 are spring-biased so as to be radially separated from each other, while their middle portions engage elastically with the outer peripheral edge at the open distal end of the outer sheath 16. Further, the injector needle 42 is disposed along the axis of symmetry of such pair of elements 241.

The respective tip ends of the plate elements 241 are somewhat widened and provided with teeth 241a on their facing sides. Tending to prevent the elements 241 from slipping when they are holding tissue inside the body cavity, these teeth 241a may be used in place of the hook-shaped tip ends as shown in FIG. 3 or 6 according to the character of the tissue to be grasped.

Now there will be described how the medical fluid is injected into a tissue 43 inside the body cavity by means of the celiac injector according to this invention.

First, at the driving section 17 of the injector 14, the slider 23 and the needle driving member 32 are pulled in the opposite direction to arrow A of FIG. 2, and held in the backward position by their corresponding locating means. Thereupon, the wire elements 41 of the claw means 40 of FIG. 3 are retreated to a position (not shown) where they are entirely hidden away in the outer sheath 16, and the injector needle 42 is held in the backward position as shown in FIG. 3.

In this state, the outer sheath 16 of the injector is inserted into the channel 13 of the endoscope 10, with its distal end forward. Then it is introduced into the body cavity, and guided to a part to be injected inside the body cavity by means of the endoscope.

Observing through the endoscope, the operator may realize that the distal end 16a of the outer sheath 16 has approached the objective part. Then, the slider 23 is slided in the direction of arrow A (FIG. 2). Thereupon, the driving force is transmitted to the claw means 40 through the transmission tube 19, and the wire elements 41 rush out from the open distal end 16a of the outer sheath, extending to the full so as to have their tip ends separated from each other or opened while in sliding contact with the rounded outer peripheral edge of the cover ring 20 by their own elasticity, as shown in FIG. 3.

Thereafter, when the tip end hooks 41a of the wire elements 41 hit against the tissue 43 at the desired part, the slider 23 is again retreated in the direction opposite to arrow A (FIG. 2). In doing this, the whole body of the injector ought to be so moved as to bring the outer sheath 16 a little closer to the tissue 43. Then, the tissue 43 is grasped by the pair of elements 41 of the claw means 40, as shown in FIG. 4. When the slider 23 is located in a forward position, the claw means 40 is temporarily fixed while it is grasping the tissue 43.

Subsequently, the needle driving member 32 is thrusted from the backward position into the forward position in the direction of arrow A. Then, the injector needle 42 is subjected to the thrusting force of the member 32 through the tube 18, thus advancing to be stabbed right into the center of the caught and fixed tissue 43, as shown in FIG. 4. Where the tissue is fully penetrated, the driving member 32 is fixed to the forward position.

Thereafter, the medical fluid to be injected is introduced from the container 36 into the supply tube 18, and then injected into the tissue 43 by means of the injector needle 42. Thus, a prescribed injecting operation is accomplished.

After the completion of the injection, the driving member 32 is retreated to draw out the needle 42 from the tissue 43 and to hide it away in the outer sheath 16. The slider 23 is once further advanced over a short distance from the fixed forward position to remove the claw means 40 from the tissue 43, and then drawn back to the backward position, where the claw means 40 is housed in the outer sheath 16.

On completion of the injection, the whole of the injector is pulled out from the channel 13 of the endoscope 10, and the whole process is finished.

According to the celiac injector of this invention, as described in detail herein, the tissue at the objective part may securely be caught by the claw means remote-controlled by the operator, and the injector needle may be stabbed positively into the tissue without involving such problems as slipping and unexpected removal. Accordingly, injections may securely be applied even to the tissue of organs in drastic motion, without involving the fear of the needle's coming off in the middle of an operation.

Moreover, the slider and the needle driving member at the driving section of the injector are temporarily fixed to the forward backward positions, so that the hold of the tissue by the claw means, as well as the penetration of the injector needle, is stabilized, improving secureness of the injecting operation.

What is claimed is:

1. In a celiac injector introduced into a body cavity by means of an intra-celiac medical instrument such as an endoscope, whereby a medical fluid is injected into celiac tissue, of the type having:
   a flexible, elongated outer sheath with an open distal end;
   a flexible medical fluid supply tube with a proximal end through which the medical fluid is introduced and capable of sliding in said outer sheath;
   an injector needle mounted on the distal end of said supply tube;
   a needle driving means connected with the proximal end of said supply tube so that said supply tube may slide relatively to said outer sheath, thereby projecting said injector needle from the open distal end of said outer sheath;
   the improvement which comprises
   a drive transmission member capable of moving in the longitudinal direction of said outer sheath within a space between said outer sheath and said supply tube;
   a driving means connected to the proximal end of said drive transmission member, whereby said member is moved relatively to said outer sheath and said supply tube; and
   a claw means connected to a distal end of said drive transmission member and capable of moving at the open distal end of said outer sheath in accordance with the operation of said driving means.

2. The celiac injector according to claim 1, wherein said claw means is formed of two or more wire elements whose proximal ends are rigidly fixed to the distal end of said drive transmission member, and whose free ends extend longitudinally and are curved so as to be separated radially from one another.

3. The celiac injector according to claim 2, wherein the middle portions of said wire elements elastically slide on the peripheral edge of the open distal end of said outer sheath while said wire elements are moving longitudinally.

4. The celiac injector according to claim 2 or 3, wherein said wire elements are so arranged as to surround said injector needle.

5. The celiac injector according to claim 1, wherein said claw means is formed of two or more narrow plate-like elements whose proximal ends are rigidly fixed to the distal end of said drive transmission member, and whose free ends each have a plurality of teeth facing one another.

6. The celiac injector according to claim 1, wherein said driving means includes a slider fixed to the respective proximal ends of said drive transmission member and said outer sheath and having on the outer peripheral surface an annular grip groove, said slider being capable of sliding relatively to grip member with a pair of finger rings.

7. The celiac injector according to claim 6, wherein a locating means for removably fixing said slider and said grip member in two separate relative positions along the sliding direction is disposed between said slider and said grip member, said claw means projecting from the open distal end of said outer sheath in one of said relative positions, and retreated in the other.

8. The celiac injector according to claim 7, wherein said locating means includes hemispherical indentations formed in the outer peripheral surface of said grip member and a ball spring-urged and held so as to be able to protrude radially into said slider and capable of engaging each said hemispherical indentation.

9. The celiac injector according to claim 6, wherein a locating means for removably fixing said needle control means with a finger ring and said grip member in two separate relative positions along the sliding direction is disposed between said needle control means and said grip member.

* * * * *